US00PP36906P2

(12) United States Plant Patent
Kordes

(10) Patent No.: US PP36,906 P2
(45) Date of Patent: Sep. 2, 2025

(54) HYBRID TEA ROSE PLANT NAMED 'KORpanimar'

(50) Latin Name: *Rosa hybrida*
Varietal Denomination: KORpanimar

(71) Applicant: W. KORDES' SÖHNE Rosenschulen GmbH & Co KG, Klein Offenseth-Sparrieshoop (DE)

(72) Inventor: Wilhelm-Alexander Kordes, Klein Offenseth-Sparrieshoop (DE)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 19/005,074

(22) Filed: Dec. 30, 2024

(30) Foreign Application Priority Data

Sep. 18, 2024 (QZ) ..... PBR 2024/2167

(51) Int. Cl.
*A01H 5/02* (2018.01)
*A01H 6/74* (2018.01)

(52) U.S. Cl.
USPC ..... Plt./135

(58) Field of Classification Search
USPC ..... Plt./135, 136, 105, 106

CPC . A01H 5/02; A01H 5/00; A01H 6/749; A01H 6/74
See application file for complete search history.

(56) References Cited

U.S. PATENT DOCUMENTS

PP33,493 P2 9/2021 Meilland

OTHER PUBLICATIONS

Kordes Roses retrieved Novelties 2024/2025 & Collections, retrieved on Mar. 18, 2025 at https://www.schetelig.com/wp-content/uploads/2025/02/Kordes-Roses_Collections-2024-2025-pakattu.pdf pp. 1-5. (Year: 2024).*
Warwaw Rose Trials retrieved on Mar. 18, 2025 at https://warsawrosetrials.pl/data/documents/5th-Warsaw-Rose-Trials-Results.pdf, 16 pp. (Year: 2025).*

* cited by examiner

*Primary Examiner* — June Hwu
(74) *Attorney, Agent, or Firm* — Panitch Schwarze Belisario & Nadel LLP; Stephany G. Small; Travis W. Bliss

(57) ABSTRACT

A new and distinct variety of hybrid tea rose plant, referred to by its cultivar name, 'KORpanimar', is described. The new variety forms in abundance on a substantially continuous basis, light apricot to cream-colored blossoms. The growth habit is bushy and upright. Semi-glossy, dark green ornamental foliage is formed. Additionally, the new variety is particularly well suited for growing as distinctive ornamentation in the landscape.

1 Drawing Sheet

Latin name of genus and species of plant claimed: *Rosa hybrida.*

Variety denomination: 'KORpanimar'.

STATEMENT REGARDING PRIOR DISCLOSURES BY THE INVENTOR

The first sale or offer for sale of the new variety was June 2024, on the Kordes Roses website. The first sale or offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of hybrid tea rose plant of the present invention was created by controlled breeding during May 2014, in Offenseth-Sparrieshoop, Germany by artificial pollination wherein two parents were crossed which previously had been studied in the hope that they would contribute the desired characteristics. The female parent (i.e., the seed parent) of the new variety was an unnamed breeder seedling (not patented). The male parent (i.e., the pollen parent) of the new variety was the 'PEAfanfare' variety (not patented).

The parentage of the new variety can be summarized as follows:

unnamed breeder seedling x 'PEAfanfare'

The seeds resulting from the above pollination were sown and small plants were obtained which were physically and biologically different from each other. Selective study resulted in the identification of a single plant of the new variety.

The new variety has been found to undergo asexual propagation in Wasco, California and Cochranville, Pennsylvania by a number of routes such as vegetative cuttings. Asexual propagation techniques in Wasco, California and Cochranville, Pennsylvania, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of hybrid tea rose plant of the present invention possesses the following combination of characteristics:

(a) forms light apricot to cream-colored blossoms, (b) exhibits a bushy and upright growth habit, and (c) provides semi-glossy, dark green foliage.

The new variety well meets the needs of the horticultural industry. It can be grown to advantage as ornamentation in parks, gardens, public areas, and residential landscapes. Accordingly, it is particularly well suited for growing in the landscape.

The new variety can be readily distinguished from its ancestors. More specifically, the new variety displays a flatter flower shape, and a less intense floral fragrance compared to the unnamed breeder seedling (i.e., the seed parent). Additionally, the new variety has a higher petal count compared to the 'PEAfanfare' variety (i.e., the pollen parent). Moreover, the new variety can be readily distinguished from non-parental related similar varieties. For example, the new variety exhibits a more compact growth habit, has a less intense floral fragrance, and forms light apricot to cream-colored flowers compared to the 'MEIROGUSTE' variety (U.S. Plant Pat. No. 33,493) which forms white-colored flowers.

The new variety has been named the 'KORpanimar' variety.

BRIEF DESCRIPTION OF THE PHOTOGRAPH

The accompanying photograph shows, as nearly true as it is reasonably possible to make the same in a color illustration of this character, a typical specimen of the new variety and blossoms of the new variety. The illustrated rose plant of the new variety was approximately three years of age and was grown outdoors in a field in Cochranville, Pennsylvania in May 2023.

Drawing—illustrates a specimen of the plant displaying flowers at varying points of opening.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms and The R.H.S. Colour Chart designation used herein represents the closest color observed on the majority of the specified botanical feature. The description is based on a four-years-old specimen of the new variety, observed during September, while growing on its own roots in a field in Cochranville, Pennsylvania.

Botanical classification: *Rosa hybrida* cultivar 'KORpanimar'.

Commercial classification: Hybrid Tea Rose.

Plant:

*Habit*.—Bushy and upright.

*Height*.—Approximately 122.0 cm on average from the top of the soil plane when growing in the ground.

*Width*.—Approximately 76.0 cm on average.

Branches:

*Stem color*.—Old wood: Green Group 138A. — young stems: Yellow-Green Group 144A with Greyed-Purple Group 183C in some areas.

*Length*.—Main stems: approximately 122.0 cm on average. — secondary stems: approximately 60.0 cm on average.

*Diameter*.—Main stems: approximately 2.0 cm on average. secondary stems: approximately 7.0 mm on average.

*Texture*.—Smooth.

*Prickles*.—Amount: few to no prickles on top half of plant; 5 to 6 prickles per internode on main stems of lower half of plant. — young prickles: length is approximately 4.0 mm on average; width is approximately 3.0 mm on average at point of attachment; and color is Greyed-Orange Group 177C. — old prickles: length is approximately 9.0 mm on average; width is approximately 1.0 cm on average at point of attachment; and color is Brown Group 200B.

Leaflets:

*Number*.—3, 5, and 7.

*Shape*.—Ovate; apex is acute to acuminate; and base is cuneate.

*Arrangement*.—Odd-pinnate.

*Margin*.—Serrate.

*Undulation*.—Moderate.

*Glossiness of upper side*.—Semi-glossy.

*Texture*.—Upper surface: smooth. — under surface: smooth.

*Venation pattern*.—Reticulate.

*Size*.—Terminal leaflet: length is approximately 5.0 cm on average; width is approximately 4.0 cm on average. — lower leaflets: length is typically 3.0 cm to 4.0 cm; width is typically 2.2 cm to 3.0 cm. — 5-Leaflet leaf: length is approximately 12.5 cm on average; width is approximately 8.5 cm on average.

Foliage:

*Young foliage*.—Upper surface color: Green Group 135A with indistinguishable venation. — under surface color: Green Group NN137B with Greyed-Purple Group N186C around margins and venation of Greyed-Orange Group 177B.

*Old foliage*.—Upper surface color: Green Group 139A with indistinguishable venation. — under surface color: Green Group 137B with indistinguishable venation.

*Petiole*.—Texture: upper surface is hispidulous; under surface is smooth. — length: approximately 3.0 cm on average. — width: approximately 1.0 mm on average. — upper surface color: Yellow-Green Group 144A. — under surface color: Green Group 138A.

*Rachis*.—Length: approximately 2.7 cm on average. — width: approximately 1.0 mm on average. — upper surface color: Brown Group 200B. — under surface color: Green Group 137D.

*Stipules*.—Length: approximately 1.5 cm on average. — width: approximately 2.0 mm on average. — margin: entire to erose. — upper surface color: Green Group 138A. — lower surface color: Green Group 137D.

Inflorescence:

*Number of flowers*.—About 20 to 25 blooms on average on a plant at once.

*Number of blossoms per stem or in a cluster*.—Typically 1 bloom per stem on average.

*Peduncle*.—Color: Mainly Green Group NN137B with some Greyed-Purple Group 183B. — diameter:

approximately 1.0 mm on average. — length: approximately 6.0 cm on average. — surface texture: hispid.

*Sepals*.—Number: 5. — upper surface color and texture: Green Group 138A and Green Group 139A, covered in short pubescence. — under surface color and texture: Green Group 139B and Yellow-Green Group 146A, puberulent. — size: length is typically 2.0 cm to 5.5 cm; width is typically 8.0 mm to 1.4 cm. — margin: entire with extensions on most sepals measuring approximately 1.3 mm in length on average and typically between 1.0 mm to 2.0 mm in width. — shape: lanceolate. — apex: acute to aristate. — base: truncate as it joins the receptacle.

*Buds*.—Shape: ovoid. — size: length is approximately 2.3 cm on average; width is approximately 1.9 cm on average. — color (when opening): Yellow-Orange Group 16B with petal margin of Orange Group 24A.

*Flower*.—Form: double, cuplike. — profile: concave as it opens, and then outer petals are convex as the bloom ages and opens further. — shape when view from top: round at initial opening, more irregularly round as petals reflex. — diameter: approximately 10.0 cm on average. — height: approximately 4.5 cm on average. — duration: on the plant approximately 10 to 12 days. — petal color when first and fully opened: upper surface of inner petals is Yellow-Orange Group 23B, upper surface of outer petals is Yellow-Orange Group 19B with a small sized basal spot of Yellow Group 12A; under surface of inner petals is Orange Group 24C, under surface of outer petals is Yellow-Orange Group 18C with a basal spot of Yellow-Orange Group 18A. — petal color at end of bloom: upper surface is White Group 155C with a small sized basal spot of Greyed-Yellow Group 162B; under surface is White Group 155C with a basal spot of Yellow Group 4A. — petals reflex one by one: yes.

*Fragrance*.—Strong sweet scent.

*Petal*.—Number: 90 on average. — drop: good. — length: typically 4.0 cm to 4.5 cm. — width: typically 2.0 cm to 4.0 cm. — overall shape: broadly obovate. — margin: entire with moderate undulation. — apex shape: rounded to slightly cuspidate. — base shape: cuneate. — texture: upper surface is smooth; under surface is smooth.

*Petaloids*.—Number: approximately 6 on average. — length: approximately 2.0 cm on average. — width: approximately 8.0 mm on average. — color: upper and under surfaces are White Group 155C with a basal spot of Yellow Group 10C on the upper surface and no basal spot on the under surface. — texture: upper surface is smooth; under surface is smooth. — margin: entire. — shape: obovate. — apex: rounded to slightly cuspidate. — base: cuneate.

*Stamen*.—Number: approximately 22. — anthers: number is approximately 22; color is Yellow-Orange Group 22A; length is approximately 4.0 mm on average; and shape is oval. — filaments: length is approximately 7.0 mm on average and color is Green-Yellow Group 1D.

*Pistils*.—Arrangement: separate and free. — number: approximately 20. — style: length is approximately 8.0 mm on average and color is Green-Yellow Group 1C and Greyed-Purple Group 183A. — stigma: diameter is approximately 1.0 mm on average; shape is fan shaped; color is Greyed-Purple Group 187B.

*Receptacle*.—Diameter: approximately 8.0 mm on average. — depth: approximately 8.0 mm on average. — shape: urn shaped. — color: Green Group 143C. — surface texture: smooth.

*Pollen*.—Amount: sparse. — color: Yellow-Orange Group 20A.

*Hips/seed*.—None observed.

Development:

*Vegetation*.—Semi-glossy, dark green, and vigorous.

*Blossoming*.—Abundant and continuous from spring through frost; typically, in bloom outdoors from May to November in Southeastern Pennsylvania.

*Resistance to diseases*.—Excellent resistance for black spot (*Diplocarpon rosae*), powdery mildew (*Podosphaera pannosa*) and rust (*Phragmidium tuberculatum*).

*Hardiness*.—Hardy to USDA Zone 6; further hardiness testing is in progress.

The new 'KORpanimar' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of hybrid tea rose plant named 'KORpanimar' characterized by the following combination of characteristics:

(a) forms light apricot to cream-colored blossoms, (b) exhibits a bushy and upright growth habit, and (c) provides semi-glossy, dark green foliage; substantially as herein shown and described.

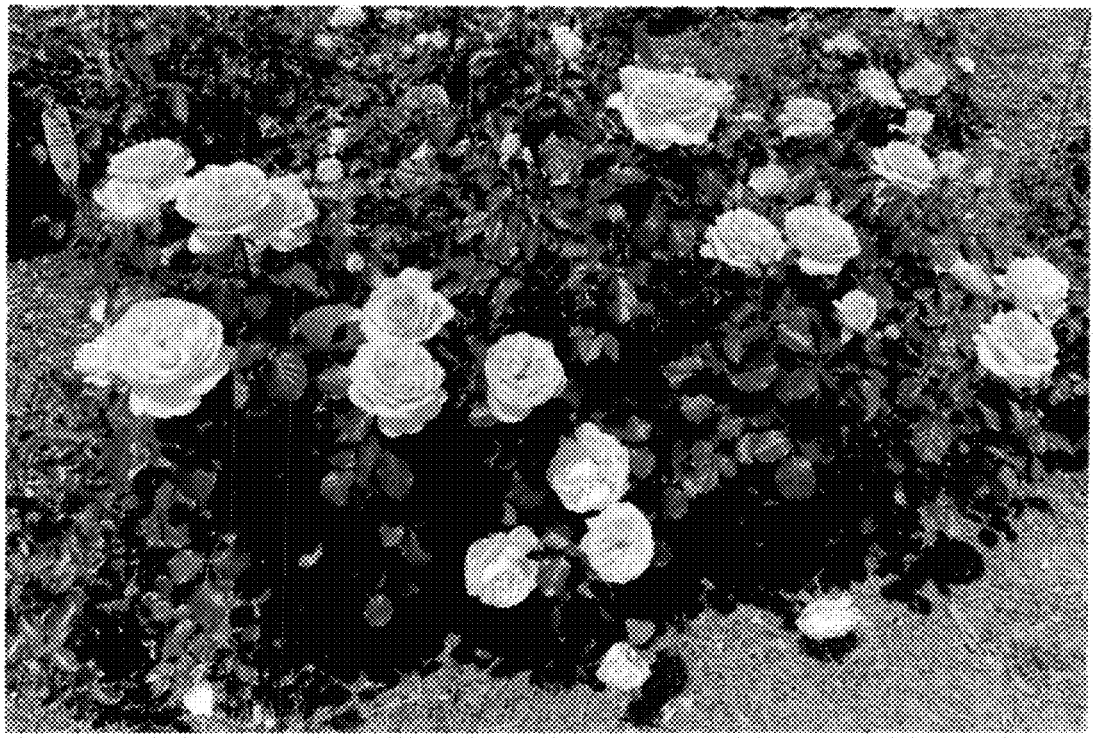

* * * * *